United States Patent [19]
Shimizu et al.

[11] Patent Number: 5,445,948
[45] Date of Patent: Aug. 29, 1995

[54] PROCESS FOR CULTURING RECOMBINANT CELLS

[75] Inventors: Norio Shimizu; Shinichi Fukuzono, both of Hitachi; Nobuko Nishimura, Katsuta; Kiyoshi Fujimori; Yoji Odawara, both of Hitachi, all of Japan

[73] Assignee: Hitachi, Ltd., Tokyo, Japan

[21] Appl. No.: 124,075

[22] Filed: Sep. 21, 1993

Related U.S. Application Data

[63] Continuation of Ser. No. 918,337, Oct. 14, 1986, abandoned.

[30] Foreign Application Priority Data

Oct. 14, 1985 [JP] Japan ................................ 60-226785

[51] Int. Cl.$^6$ ...................... C12P 21/00; C12N 15/71; C12N 15/03
[52] U.S. Cl. .................................. 435/69.7; 435/69.1; 435/252.33; 435/252.3; 435/91.1; 435/162; 536/23.4; 935/38; 935/39; 935/43; 935/73
[58] Field of Search ...................... 435/69.1, 69.7, 69.2, 435/69.3, 69.4, 69.5, 69.6, 69.51, 252.3, 252.33, 320.1, 172.3, 207, 102; 935/2, 22, 29, 38, 39, 40, 43, 44, 47, 60, 73

[56] References Cited

U.S. PATENT DOCUMENTS

| | | | |
|---|---|---|---|
| 4,021,304 | 5/1977 | Shimamatsu et al. | 435/3 |
| 4,831,120 | 5/1989 | Auiv et al. | 530/399 |
| 4,891,310 | 1/1990 | Shimizu et al. | 435/3 |

FOREIGN PATENT DOCUMENTS

0022341  1/1981  European Pat. Off. .

OTHER PUBLICATIONS

Moat et al. 1988. in: *Microbiol Physiology*, Second Edition, John-Wiley & Sons New York, p. 449.
Herskowitz 1977. in: *Principles of Genetics*, Second Edition. Macmillan Publ. Co., New York pp. 210–239, 487–488, 480–485.
*Hackh's Chemical Dictionary* (Fourth Edition), 1969., Grant, J. (ed.) McGraw-Hill Book Co., New York, p. 575.
Watson, J. D. 1987, in: *Molecular Biology of the Gen.* Benjamin/Cummings Publ. Co., Menlo Park, Calif. p. 313.
Gerhardt et al. (eds.) in: *Manual of Methods for General Bacteriology*, Am. Soc. Microbiology. Washington, D.C. pp. 71,72, 79–84, 113, 166, 267–270, 247–249, 172–174, 372, 329, 299–309, 68–69, 70.
Maiorella et al. 1983. Biotechnol. Bioengr. XXV, 103–121.
Maniatis et al. 1982, in: *Molecular Cloning* A Laboratory Manuel. Cold Spring Harbor Laboratory, N.Y. pp. 404–433.
Fukuda 1978. Pat. Abstr. Japan. 3(72), 838 C78.
Edman et al. 1981 Nature 291, 503–506.
Soktoer et al. 1985. Mikrobiologiya 54, 740–744.
Yanofsky et al. 1984. J. Bacteriol. 158, 1018–1024.
Smirnova et al. 1985 (Translation of Smirnova et al. 1985 Mikrobiologa 54, 252–256).
J. Microbiol. 54, 205–209. Plenum Press.
Yano et al. 1980. J. Femment. Technol. 58, 259–266.
Mori et al. 1979, J. Chem. Engr. Japan 12, 313–319.
Landwall et al. 1977. J. Gen. Microbiol. 103, 345–352.
*The Merck Index* 10th Edition (Windholz, eds.) 1983. Merck & Co. Inc. Rahway, N.J., pp. 85–86.

*Primary Examiner*—Christopher S. F. Low
*Attorney, Agent, or Firm*—Antonelli, Terry, Stout & Kraus

[57] ABSTRACT

This invention relates to an efficient process for culturing recombinant cells which comprises a step of removing a cell proliferation inhibiting substance and/or a substance which inhibits induction of the desired product and a step of inducing production of the desired product.

4 Claims, 9 Drawing Sheets

CULTURE TIME (h)

PROCESS FOR CULTURING RECOMBINANT CELLS

This application is a Continuation application of application Ser. No. 918,337, filed Oct. 14, 1986, abandoned.

TECHNICAL FIELD

This invention relates to an efficient process for culturing recombinant cells which can be employed when cells having an objective gene from an animal, plant, microorganism or the like introduced thereinto are cultured, and the objective gene is expressed, followed by collecting the resulting product.

BACKGROUND OF THE INVENTION

Recently, there has been developed a genetic recombination technique comprising using host cells containing complex DNA (deoxyribonucleic acid) composed of their vector plasmid or the like and a gene inserted thereinto having information sequence for a useful product, and allowing said cells to produce a large amount of the useful product. Human interferon and insulin, etc. are already being produced by using this technique, and *Escherichia coli*, yeasts, *Bacillus subtilis*, Actinomyces, animal cells, plant cells, etc. have heretofore been utilized as the host.

However, there has not yet been developed any process for industrially producing a large amount of a desired product by using recombinant cells having an objective gene, and, therefore, an efficient process for culturing recombinant cells is desired to be developed as soon as possible.

As one method for allowing recombinant cells to produce a large amount of a desired product, a rise in cell concentration in culture broth is considered. However, even when a substrate is fed in order to raise the cell concentration, cell growth stops in the course of culture and it becomes difficult to raise the cell concentration. Therefore, there has been provided a process in which in order to remove a cell growth inhibiting substance which causes the stop of cell growth, a culture broth is taken out intermittently or continuously and cells are recovered by centrifugation and charged into a culture tank again (Japanese Patent Application Kokai (Laid-Open) No. 29985/78). This process is intended for culturing yeasts to produce a large amount of cells themself and is not a process for culturing cells having complex DNA for allowing the cells to produce a desired product. In cultivation of baker's yeast, there is known a process comprising detecting the production of ethanol by measuring the respiratory quotient, feeding a substrate, and thereby raising the yeast concentration (Japanese Patent Application Kokai (Laid-Open) Nos. 36983/82 and 78584/83). However, this culture process is not a process for culturing cells having complex DNA.

On the other hand, as a process for culturing cells having complex DNA, there has been proposed a process in which cells are cultured at a temperature lower than the optimum growth temperature of the cells (Japanese Patent Application Kokai (Laid-Open) No. 141796/83). However, this culture process was developed without consideration of removal of the cell growth inhibiting substance which caused the stop of cell growth.

SUMMARY OF THE INVENTION

An object of this invention is to provide an efficient process for culturing cells having complex DNA which permits production of a large amount of a desired product.

Another object of this invention is to provide an efficient process for fed-batch culture or continuous culture of *E. coli* having complex DNA.

Further another object of this invention is to provide an efficient process for fed-batch culture or continuous culture of yeast, *Bacillus subtilis*, Actynomyces, animal cells or plant cells having complex DNA.

The above-mentioned objects and advantages of this invention can be achieved by the following culture process.

That is to say, this invention is related to a process for culturing recombinant cells by culturing cells having complex DNA and possessing an ability to produce a desired product, causing expression of an objective gene, and collecting the resulting desired product, characterized by the improvement which comprises, at least one step selected from the group consisting of (a) a step of substantially removing a cell growth inhibiting substance, and (b) a step of substantially removing a substance which inhibits induction of the desired product; and (c) a step of inducing production of the desired product.

DETAILED DESCRIPTION OF THE INVENTION

This invention is applicable to any cell having complex DNA and possessing an ability to produce desired product, namely, any cell having complex DNA comprising an objective gene and a promoter. Such a cell includes, for example, *E. coli* having an ability to produce $\beta$-galactosidase ($\beta$-gal); recombinant *E. coli* capable of producing interferon or hormones such as insulin; recombinant animal cells capable of producing glcocorticoid hormones; and recombinant yeasts, *Bacillus subtilis*, Actynomyces, plant cells and the like which have an ability to produce a useful product.

The culture process of this invention involves at least one step selected from the group consisting of (a) a step of removing a cell growth inhibiting substance, and (b) a step of removing a substance which inhibits induction of a desired product. These steps are explained below by taking the case of E. coli.

As an embodiment of the highly efficient process for culturing recombinant cells of this invention, there is shown below a culture process using E. coli strain HB 101 having complex plasmid pTREZ1 comprising tryptophan (trp) promoter and β-galactosidase (β-gal) gene joined therewith.

Figure 1A:
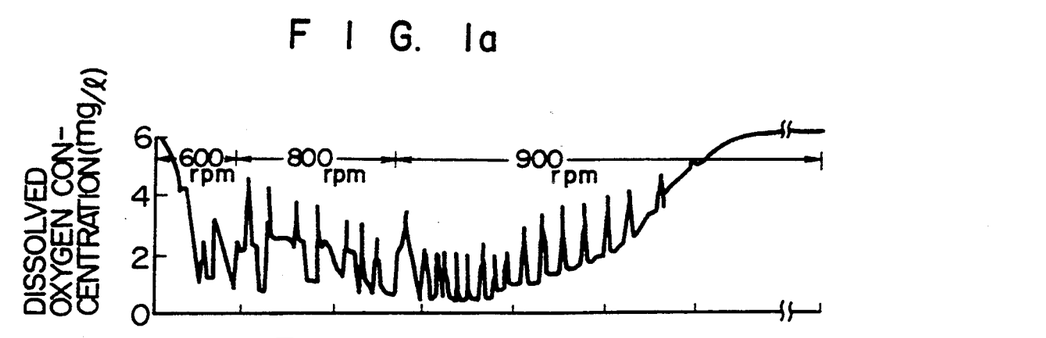
FIG. 1 is graphs showing results of a example of fed-batch culture of recombinant cells.
Figure 1B:
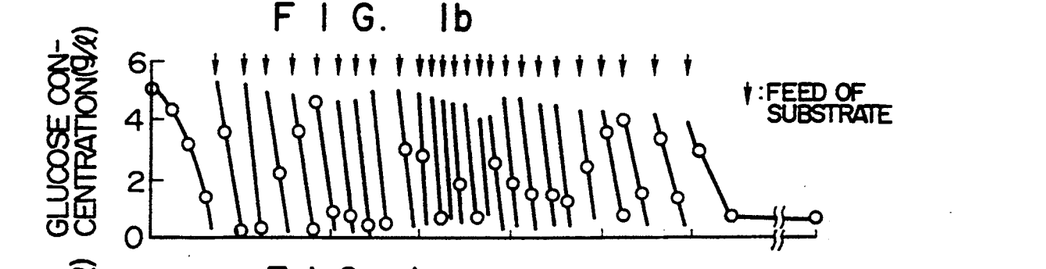
Figure 1C:
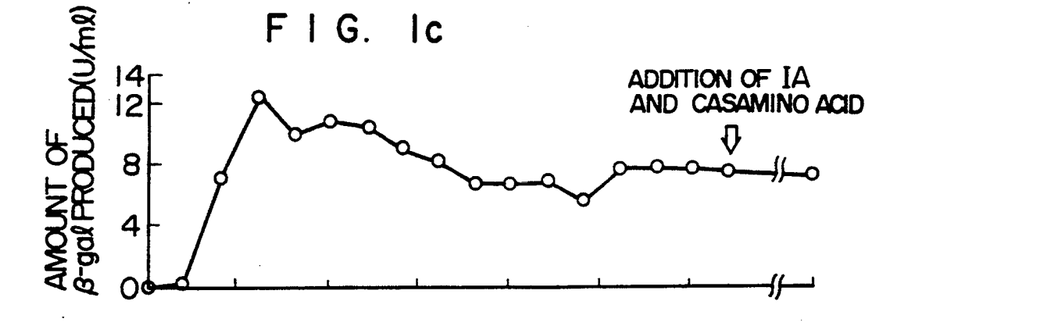
Figure 1D:
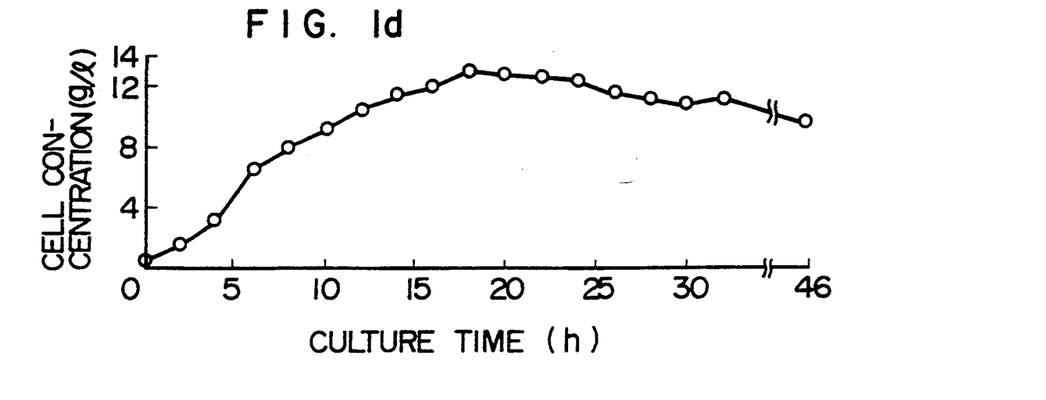
Figure 2:
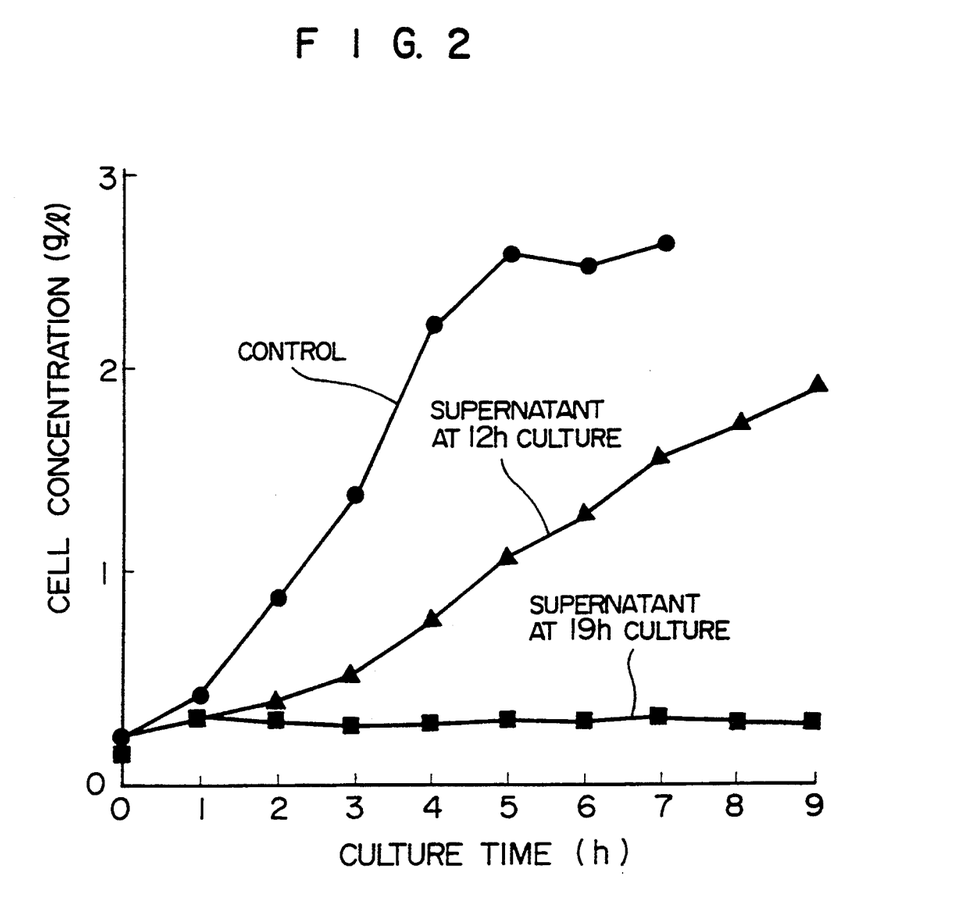
FIG. 2 shows inhibition of cell growth by a cell growth inhibiting substance in culture broth.

The results of fed-batch culture of recombinant E. coli are shown in FIG. 1. Glucose and casamino acid medium as substrate were fed with the guidance of a rise in dissolved oxygen concentration. The cell concentration reached 13.1 g/liter at 18 hours of culture, but at this time, the cell growth stopped. 3-β-Indoleacrylic acid (IA) as inducing agent and casamino acid as nutrient were added at 32 hours of culture for induction of β-gal. production, but no β-gal. production was induced. Thus, the stop of cell growth seemed to be due to the presence, in culture supernatant, of substances which inhibit cell growth or β-gal. production. Therefore, fresh medium and fresh cells were added to culture supernatant at 12 hours of culture at which cell growth still continued and to culture supernatant at 19 hours of culture at which the cell growth had already stopped, and the cells were cultured. The results obtained are shown in FIG. 2. In the case of the culture supernatant at 19 hours of culture, the cells did not grow at all, and in the case of the culture supernatant at 12 hours of culture, cell growth was so low that the specific growth rate was about one-half of that measured for a control. On the other hand, when frozen and stored cells were inoculated into fresh medium in order to examine the growing activity of cells, the specific growth rates of cells at 12 hours of culture and cells at 19 hours of culture were substantially the same as that measured for a control, and thus the growing activity of cells was not lowered. Further, β-gal. production was induced by addition of an inducing agent. From these facts, it was found that with a progress of culture, there were accumulated substances which inhibited cell growth or induction of β-gal. production.

These investigation results indicate that for stimulating growth of recombinant cells and raising the cell concentration, it is important to remove the cell growth inhibiting substance accumulated in culture broth and/or to remove the substance which inhibits induction of a desired product.

Therefore, the present inventors further conducted closer investigation on the cell growth inhibiting substance and the substance which inhibits induction of a desired product.

Figure 3:
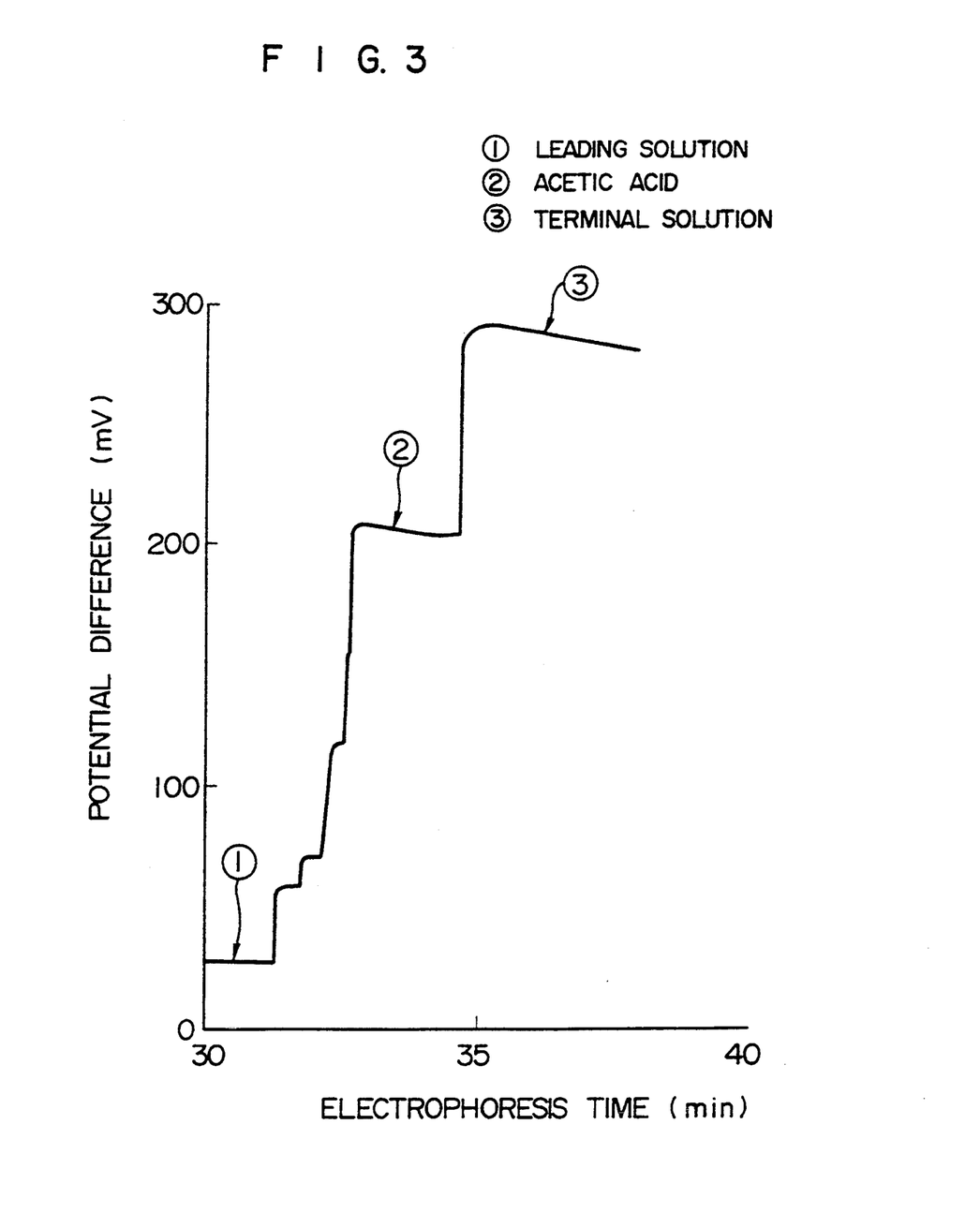
FIG. 3 shows results of analysis for acetic acid by means of a isotachophoretic analyzer.

In detail, in the above-mentioned cultivation of E. coli, culture supernatant at 19 hours of culture after the stop of cell growth was collected, and separation therefrom of the cell growth inhibiting substance was investigated. There was examined whether or not a liquid obtained by fractionating the culture supernatant according to molecular weight by using a ultrafilter membrane having a cut-off molecular weight of 1,000 inhibited cell growth. The fraction of molecular weight of 1,000 or less inhibited cell growth, and from this fact it was indicated that the inhibiting substance has a low molecular weight. Next, ionic substances were separated from said fraction by using an anion-exchange resin IRA-400 and a cation-exchange resin IR-120B and examined for their effect on cell growth to find that an anionic substance inhibited cell growth. From this fact, the cell growth inhibiting substance was found to be a low-molecular-weight, anionic substance and was assumed to be an organic acid which was well known to be secreted from cells. Accordingly, the liquid containing the low-molecular-weight, anionic substance was analyzed for organic acids by using an isotachoproetic analyzer. The analysis result is shown in FIG. 3. Electrophoresis was carried out at an electrophoresis current of 100 μA by using a 0.01M β-alanine hydrochloride solution as a terminal solution. As a result of a comparison with the components of culture medium, it was found that acetic acid ② was accumulated at a high concentration of 33 g/liter. When the corresponding amount of acetate was added to fresh medium and culture was carried out, cell growth was inhibited. This fact proved that a substance which played the most important role in the inhibition of cell growth was acetic acid. Furthermore, analysis of the culture supernatant by using a gas chromatograph also confirmed that said substance was acetic acid.

It is known that with a progress of culture, microorganisms, animal cells and plant cells secrete organic acids, but it is not known at all that among organic acids, acetic acid is produced in a large amount and inhibits cell growth, and this is a finding obtained at first by the present inventors.

Figure 4A:
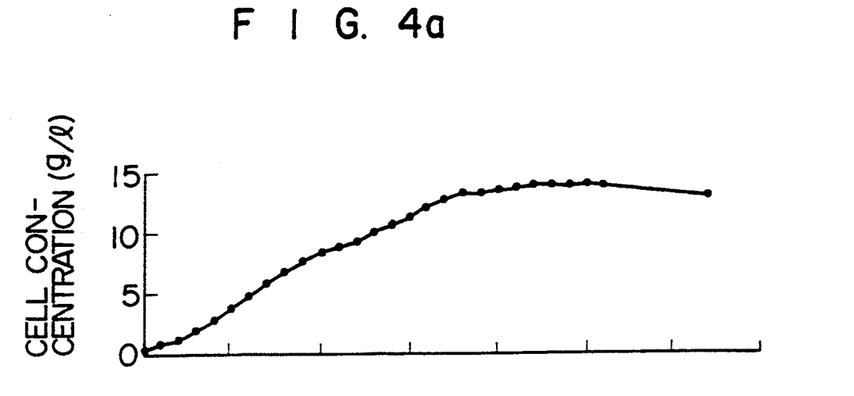
FIG. 4 shows changes dependent on time of acetic acid concentration, specific growth rate and cell concentration in fed-batch culture of recombinant *E. coli*.
Figure 4B:
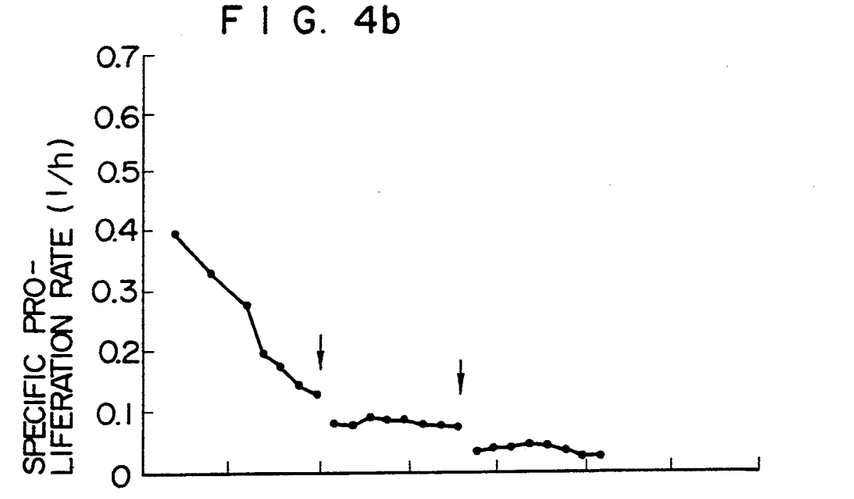
Figure 4C:
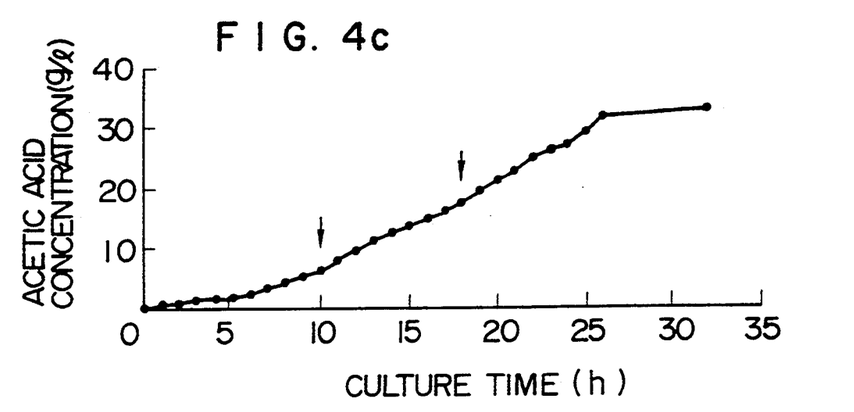

The relationship between cell growth and the amount of organic acids, particularly acetic acid accumulated in cluture broth was investigated. In FIG. 4 is shown the changes dependent on time of cell concentration, specific growth rate per hour and acetic acid concentration in culture broth which took place when glucose and casamino acid medium were continuously fed from 4 hours and 15 minutes after the initiation of cultivation of recombinant E. coli. As shown by the arrows, rapid changes in the specific growth rate were observed between at 10 hours of culture and at 11 hours of culture and between at 18 hours of culture and at 19 hours of culture. The cell growth rate after 19 hours of culture became very low, suggesting that cell growth stopped substantially. The acetic acid concentration was 6 g/liter at 10 hours of culture and 17 g/liter at 18 hours of culture. From this fact, it can be seen that the acetic acid concentration in culture broth should be controlled so as to be at most 17 g/liter or less, preferably 6 g/liter or less. In other words, the cell growth inhibiting substance can be removed by keeping the acetic acid concentration in culture broth at 17 g/liter or less, more preferably 6 g/liter or less.

Furthermore, it has been found that in causing expression of a gene by adding an inducing agent, IA addition causes no β-gal. production at an acetic acid concentration of 8 g/liter but induces β-gal. production at acetic acid concentration of 3 g/liter or less (see Example 3 and Comparative Example 1). That is to say, the substance which inhibits induction of a desired product can be removed by keeping the acetic acid concentration in culture broth at preferably 3 g/liter or less.

From the above results as well as the fact that organic acids act as the cell growth inhibiting substance and the well-known fact that Bacillus subtilis, Actynomyces, yeasts, animal cells, plant cells and the like show substantially the same behaviors as those of E. coli, the following can be understood.

Cultivation of cell such as E. coli, yeasts, Bacillus subtilis, Actynomyces, animal cells, plant cells and the like having complex DNA and possessing an ability to produce an desired product requires (a) a step of removing the cell growth inhibiting substance, preferably organic acids, more preferably acetic acid, and/or (b) a step of removing the substance which inhibits induction of a desired product, preferably organic acids, more preferably acetic acid (namely, a step of adjusting the concentration of preferably organic acids, more preferably acetic acid so as to be lower than that attained in the step (a)). In this invention, a culture process involving both the steps (a) and (b) is preferred. It is preferable to adjust the concentration of organic acids in culture broth to about 17 g/liter or less by the process (a) and to about 3 g/liter or less by the process (b).

The cell growth inhibiting substance and the substance which inhibits induction of a desired product include, for example, organic acids such as lactic acid, formic acid and the like besides acetic acid. Other examples of the cell growth inhibiting substance are sugars, salts, etc. Other examples of the substance which inhibits induction of a desired product are inhibitors to the respective promoters such as tryptophan promotor, lactose promotor, $P_L$ of $\lambda$ phage, etc.

In this invention, as methods for removing the cell growth inhibiting substance or the substance which inhibits induction of a desired product, there are employed, for example, method comprising taking out a part of culture broth, recovering cells by centrifugation, and returning the obtained cell to a culture tank; a method using a permeable membrane, a ultrafilter membrane or the like which is employed when the inhibiting substance has a low molecular weight; and a method using an ion exchange resin. These methods may be practised continuously.

The culture process of this invention requires essentially (c) a step of inducing production of a desired product, in addition to the above process (a) and/or process (b). As a method for inducing the production of a desired product, there is employed a method which comprises adding an inducing agent for a promoter contained in the complex DNA in cells. That is to say, for example, in the case of trp. promoter, addition of 3-$\beta$-indoleacrylic acid (IA) is effective, and in the case of lac. promoter and tac. promoter, addition of isopropyl-$\beta$-D-thiogalactoside (IPTG) is effective. As another method, for example, elevation of the temperature of culture broth is effective for $P_L$ promoter.

The process (c) is preferably practised subsequently to at least one of the above processes (a) and (b). The step (c) may be carried out continously.

The culture process of this invention preferably involves (d) a step of promoting cell growth, together with the above step (c). As a method for carrying out the step (d), there is used a method which comprises adding a nutrient suitable for cells used. As the nutrient, for example, casamino acid composed of a mixture of amino acids, amino acids, glucose, yeast extract, bouillon and the like are effective. The step (d) can also be carried out continously.

Particularly when applied to fed-batch culture or continuous culture, the culture process of this invention described above permits very efficient cultivation of cells having complex DNA, and hence production of a large amount of a desired product. The culture process of this invention is effective particularly in culturing $E.$ $coli.$ As methods for carrying out the above processes (a), (b), (c) and (d), conventional methods may be selected depending on host cells used, inhibiting substances, and a desired product to be produced.

Figure 9:
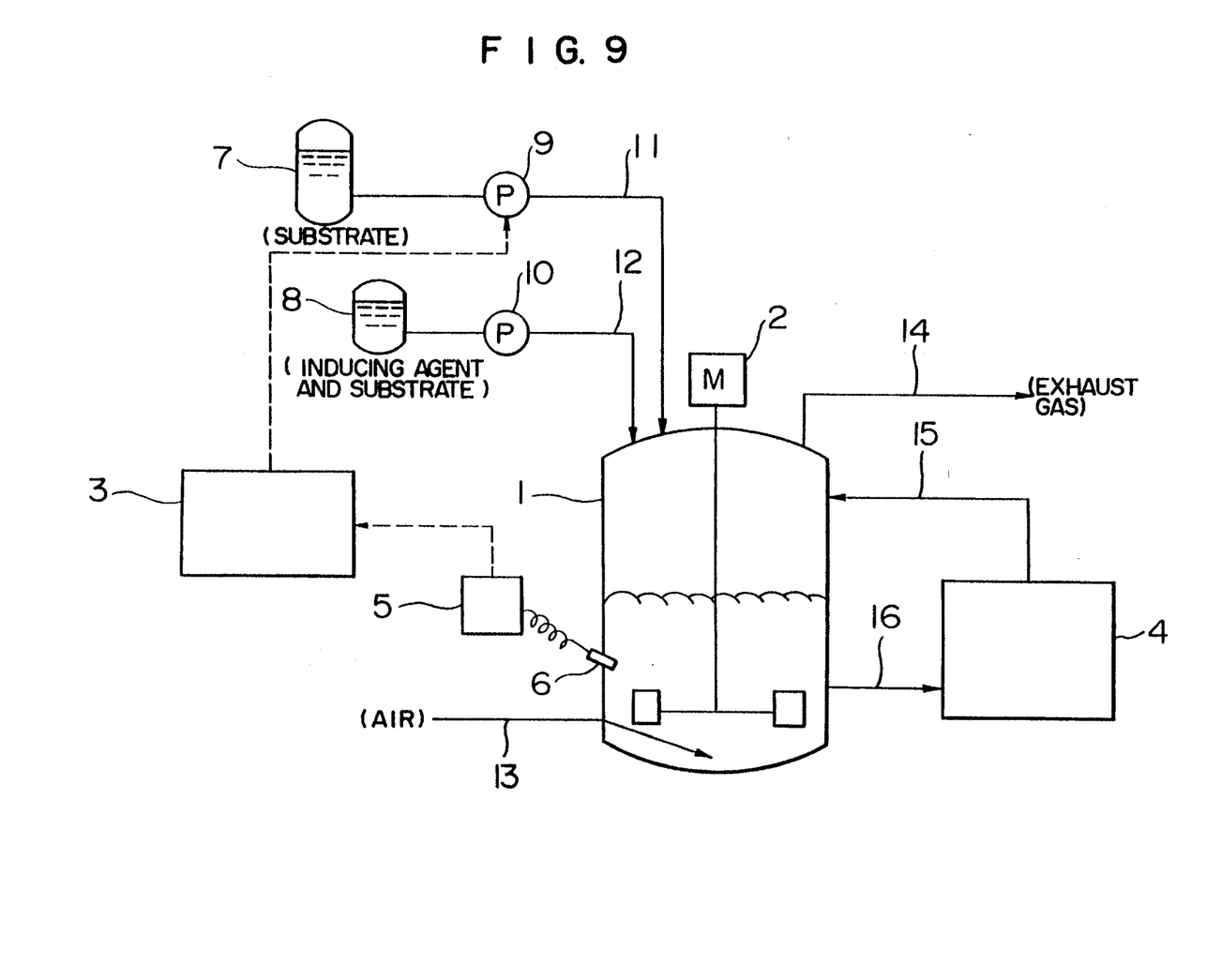
FIG. 9 is a schematic ,illustration of example of the culturing apparatus of this invention.

Next, one example of apparatus necessary for practicing the process of this invention is shown in FIG. 9. A culture medium and cells are placed in a culture tank 1, and recombinant cells are cultured while blowing air into the culture tank 1 through a conduit 13 and stirring the culture broth by means of a stirrer 2. In this case, the dissolved oxygen concentration of the culture broth at each stage is measured by means of a dissolved oxygen sensor 6 and a dissolved oxygen meter 5 both placed in the culture tank 1. The measurement data are sent to a controller 3, which monitors the change of the dissolved oxygen concentration and transmits signals to a metering pump 9 at the time of a rapid rise of the dissolved oxygen concentration to feed substrate from a substrate tank 7. After culture for a definite period of time, a part of the culture broth is taken out through a conduit 16, and inhibiting substances are removed therefrom by means of an inhibiting substance removing device 4, after which the cell suspension thus obtained is returned to the culture tank through a conduit 15. When the cell concentration reaches a high value, inhibiting substances are similarly removed by means of the inhibiting substance removing device 4, after which an inducing agent and substrate are added from an inducing tank 8 by means of a metering pump 10 to induce production of a desired product, whereby mass production of the desired product is carried out. It is preferable to equip the culture tank 1 with a device for measuring the acetic acid concentration. The desired product produced inside or outside the cells is made into a final product by separation and purification.

As described above in detail, according to this invention, merely by removing the cell growth inhibiting substance and/or the substance which inhibits induction of a desired product and inducing the production of a desired product during culture, a high cell concentration can be attained and production of a large amount of the desired product can be induced.

This invention is explained below in detail with reference to Examples which are not by way of limitation but by way of illustration.

EXAMPLE 1

Cells: $E.$ $coli$ strain. HB 101 having complex plasmid pTREZ1 (deposited as FERM BP-8136).

Initial medium: M9-casamino acid medium, which was composed of 1 g of $NH_4Cl$, 6 g of $Na_2HPO_4$, 3 g of $KH_2PO_4$, 5 g of NaCl, 0.1 g of $MgSO_4.7H_2O$, 15 mg of $CaCl_2.2H_2O$, 0.1 g of thiamine hydrochloride, 0.1 g of proline, 0.01 g of tryptophan, 5 g of glucose, 2.5 g of casamino acid, 1.5 g of yeast extract and 1 l of distilled water, and had a pH of 7.0. To the medium was added 50 mg/liter of ampicillin (Ap) in order to grow only $E.$ $coli$ having complex plasmid.

Medium for feeding: this medium was composed of 200 g of glucose, 4 g of proline, 100 g of casamino acid, 60 g of yeast extract, 0.4 g of tryptophan and 1 liter of distilled water, and had a pH of 7.0.

Culture conditions: $E.$ $coli$ having complex plasmid was inoculated into four 500-ml shaker flasks each containing 50 ml of M9-casamino acid medium and cultured overnight by means of a shaker under the conditions of a stroke of 7 cm, a oscillation of 115 times/min. and a temperature of 37° C. Into a 5-liter jar fermenter containing M9-casamino acid medium was inoculated 200 ml of the seed culture thus obtained, and culture was initiated at an initial volume of culture broth of 2 liters, at 37° C., at pH 7.0 and at an aeration rate of 2 liters/min. The change of the dissolved oxygen concentration during culture was detected, and at the time of a rapid rise of the dissolved oxygen concentration, 50 ml of feeding medium was fed.

Figure 5A:
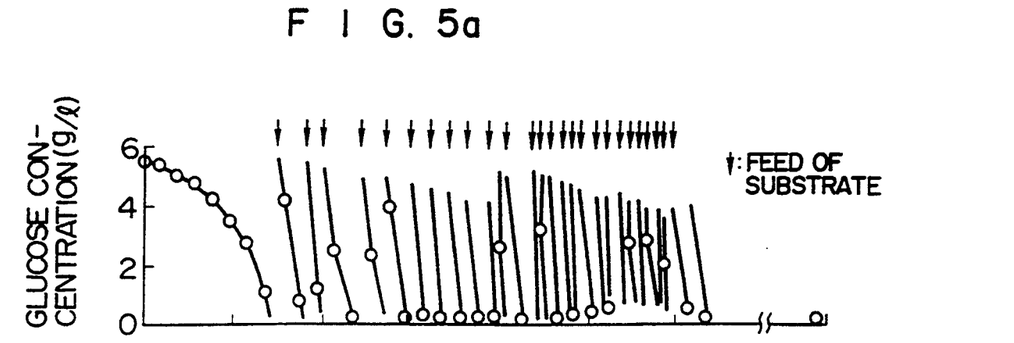
FIG. 5 shows results of culturing cell in case of removing a culture supernatant during fed-batch culture of recombinant cells.
Figure 5B:
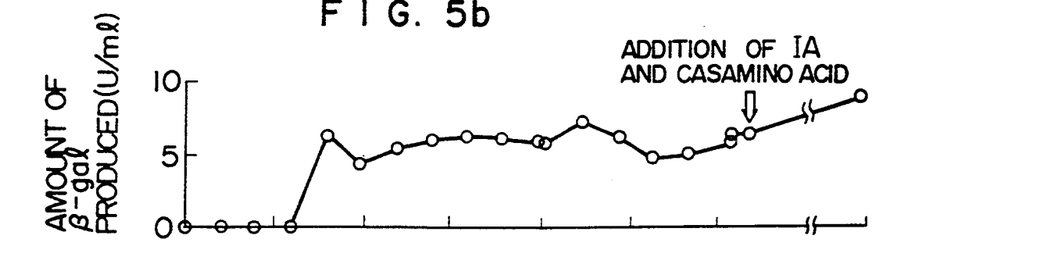
Figure 5C:
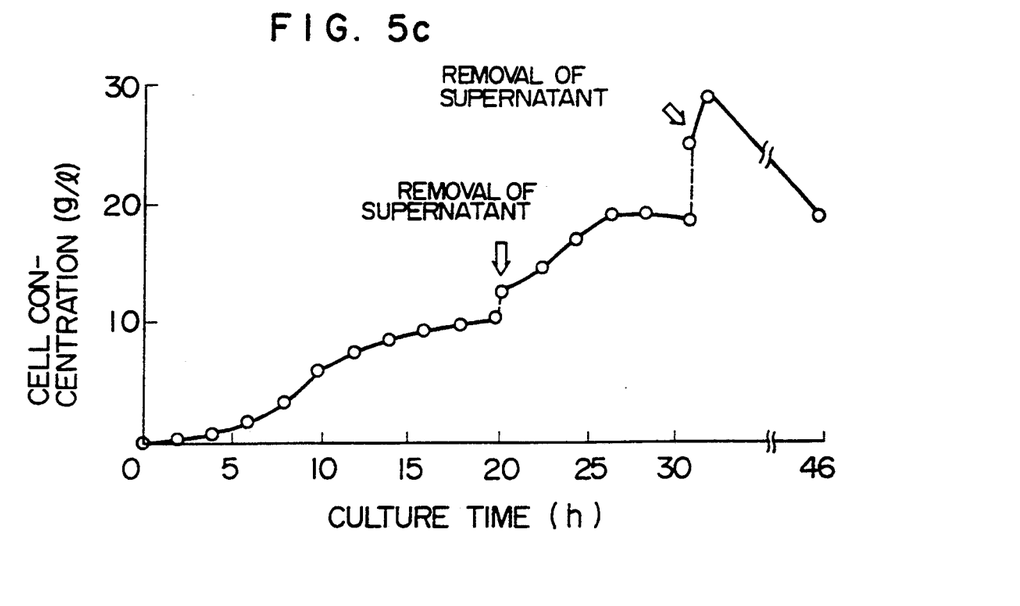

As shown in FIG. 5, when culture supernatant was removed by centrifugation at 20 hours of culture and cells were recovered and re-suspended in fresh medium, followed by feeding substrate, the cell concentration reached a high value of 19.2 g/liter at 28.5 hours of culture. Cells were recovered again by centrifugation at 31 hours of culture and then suspended in fresh medium, and when glucose was consumed, 50 mg/liter of IA and 25 mg/liter of casamino acid were added. As a result, the amount of $\beta$-gal. produced was increased to 1.4 times that attained before the addition.

EXAMPLE 2

There was conducted repeated fed-batch culture in which culture supernatant was removed by centrifugation during culture in order to remove acetic acid, i.e., a cell growth inhibiting substance accumulated in culture broth.

Cells: *E. coli* strain HB 101 having complex plasmid pTREZ1.

Initial medium: M9-casamino acid medium, which was composed of 1 g of NH$_9$Cl, 6 g of Na$_2$HPO$_4$, 3 g of KH$_2$PO$_4$, 5 g of NaCl, 0.1 g of MgSO$_4$.7H$_2$O, 15 mg of CaCl$_2$.2H$_2$O, 0.1 g of thiamine hydrochloride, 0.1 g of proline, 0.01 g of tryptophan, 5 g of glucose, 2.5 g of casamino acid, 1.5 g of yeast extract and 1 liter of distilled water, and had a pH of 7.0. To the medium was added 50 kg/liter of ampicillin (Ap)in order to grow only *E. coli* having complex plasmid.

Medium for feeding: this medium was composed of 200 g of glucose, 4 g of proline, 100 g of casamino acids, 60 g of yeast extract, 0.4 g of tryptophan, 1 g of ampicillin and 1 liter of distilled water, and had a pH of 7.0.

Culture conditions: *E. coli* having complex plasmid was inoculated into four 500-ml shaker flasks each containing 50 ml of M9-casamino acid medium and cultured overnight by means of a shake culture machine under the conditions of a stroke of 7 cm, a oscillation of 115 times/min and a temperature of 37° C. Into a 5-liter jar fermenter containing M9-casamino acid medium was inoculated 200 ml of the seed culture thus obtained, and culture was initiated at an initial volume of culture broth of 2 liters, at 37° C., at pH 7.0 and at an aeration rate of 3 liters/min. The change of the dissolved oxygen concentration during culture was detected and at the time of a rapid rise of the dissolved oxygen concentration, 50 to 150 ml of medium for batch feeding was added. Acetic acid in the culture broth was determined by introducing culture supernatant into a gas chromatograph filled with Unicarbon A-300 60/80, and culture supernatant was removed with the guidance of the time at which about 10 g/liter of acetic acid was accumulated. The removal of culture supernatant was conducted by centrifuging the culture broth at 6,000 r.p.m. for 10 minutes, and cells were recovered and suspended in fresh initial medium to make a total volume of 2 liters, after which culture was initiated again.

Figure 6A:
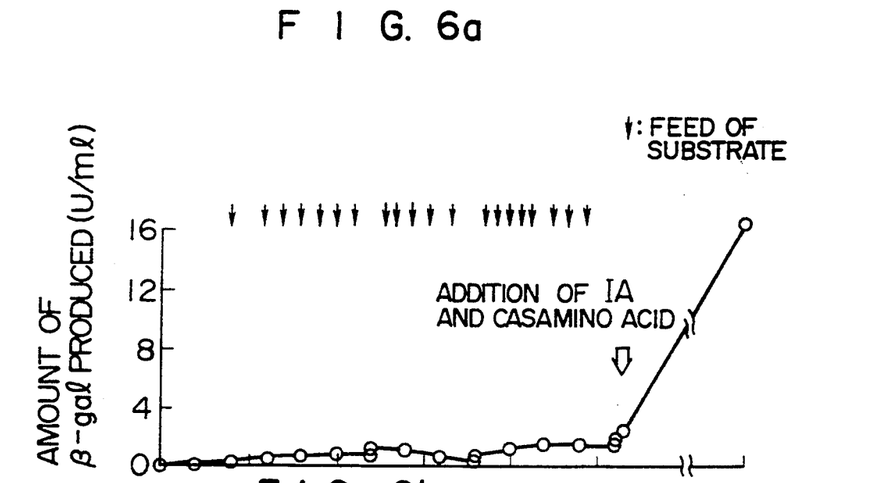
FIG. 6 shows results of repeated fed-batch culture of recombinant *E. coli*.
Figure 6B:
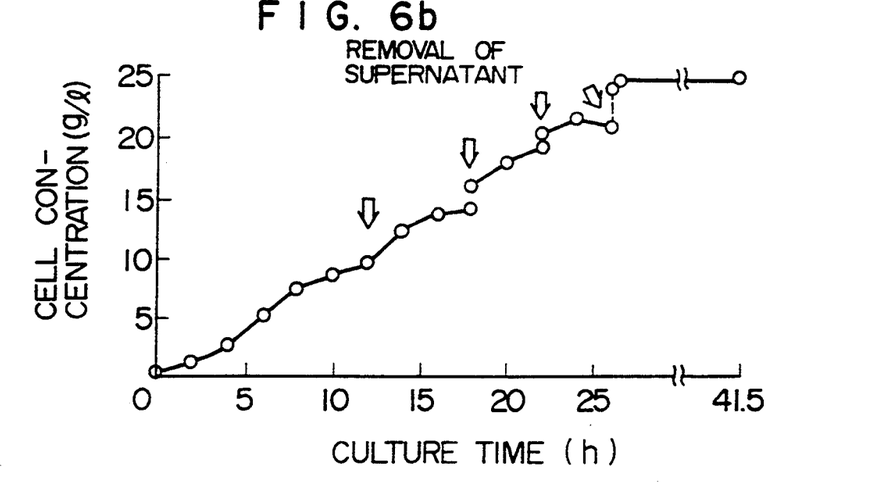

Results: As shown in FIG. 6, when fed-batch culture was carried out while removing culture supernatant by centrifugation at 12, 18, 22 and 26 hours of culture, the cell concentration reached a high value of 21.3 g/liter based on dried basis. When 50 mg/liter of IA as inducing agent and 25 g/liter of casamino acid as material for $\beta$-gal. production were added at 26.5 hours of culture, the amount of $\beta$-gal. produced reached 16 U/ml (which was about 8 times the amount of $\beta$-gal. produced before the IA addition) at 41.5 hours of culture.

Thus, according to this invention, cells can be cultured so as to attain a high cell concentration by removing acetic acid, i.e., a cell growth inhibiting substance by centrifugation, and a large amount of a useful product can be obtained by causing expression of an objective gene by using an inducing agent.

EXAMPLE 3

Since cell growth was stopped by acetic acid, i.e., a cell growth inhibiting substance accumulated in culture broth, culture supernatant was removed by centrifugation, after which an inducing agent was added to cause $\beta$-gal. production.

Fed-batch culture was carried out by employing the same cells and culture conditions as in Example 1, except that no removal of culture supernatant by centrifugation was conducted during cell growth.

Figure 7A:
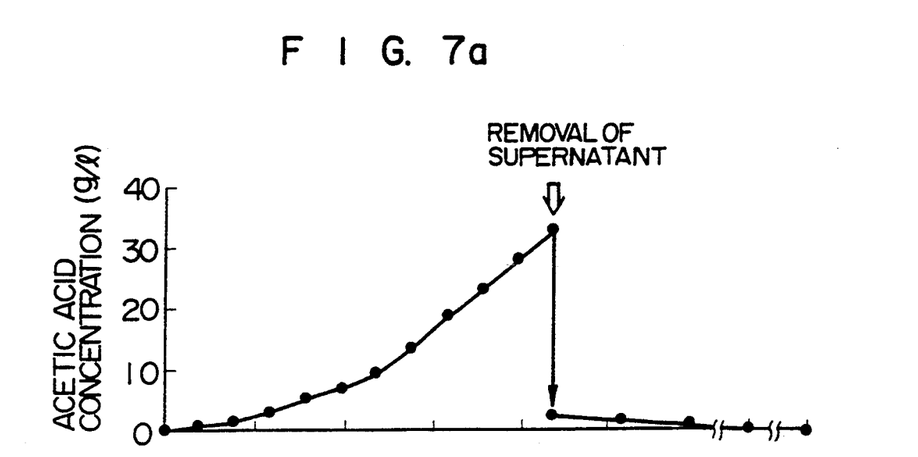
FIG. 7 shows results of $\beta$-gal production in case of removing acetic acid in fed-batch culture of recombinant *E. coli*.
Figure 7B:
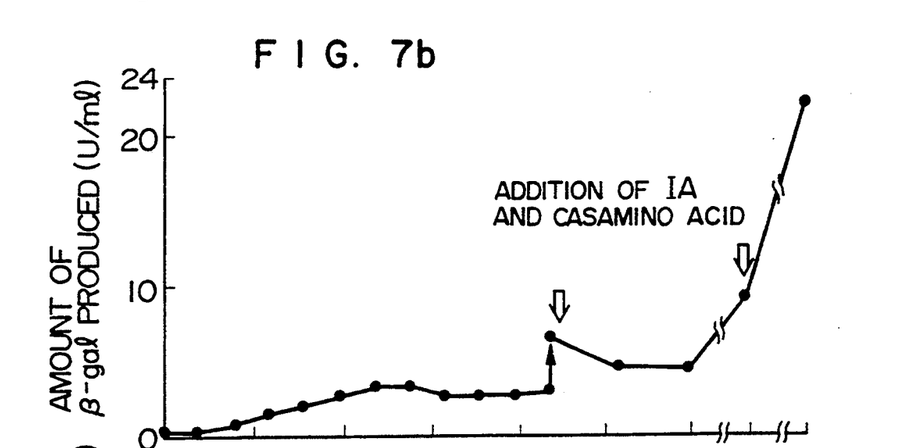
Figure 7C:
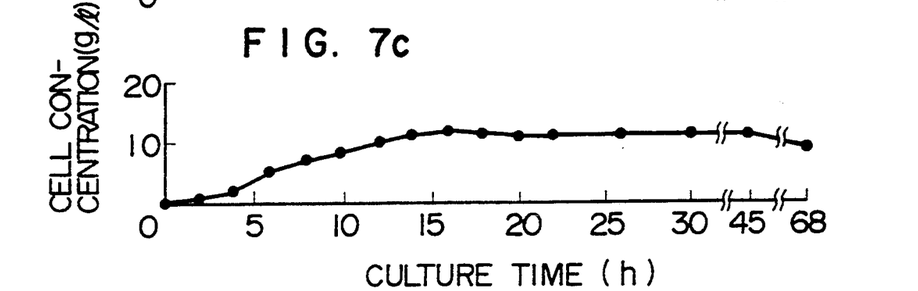

Results: As shown in FIG. 7, cell growth stopped substantially after 14 hours of culture at which the acetic acid concentration in culture broth became 14 g/liter. Therefore, feed of substrate resulted in only production of a large amount of acetic acid. Therefore, culture supernatant was removed by centrifugation at 22 hours of culture, after which cells were re-suspended in fresh medium and culture was initiated. When 50 mg/liter of IA and 25 g/liter of casamino acid were added 30 minutes after the initiation of culture (by this time, glucose as substrate had been consumed), 9.1 U/ml of $\beta$-gal. was produced at 45 hours of culture. When IA and casamino acid were added at this time in the same amount as in the above addition, $\beta$-gal. was produced in a large amount of 22.1 U/ml at 68 hours of culture. The acetic acid concentration in culture broth in this case was 2.8 g/liter at the time when culture was initiated again after the removal of culture supernatant but then decreased gradually and became substantially zero at 68 hours of culture.

Thus, when acetic acid, i.e., a cell growth inhibiting substance and a substance which inhibits induction of the desired product, is removed according to this invention, expression of an objective gene can be caused by using an inducing agent, so that it becomes possible to obtain a large amount of a useful product.

Comparative Example 1

Culture was carried out without removing acetic acid, i.e., a cell growth inhibiting substance accumulated in culture broth, and an inducing agent (IA) was added.

Fed-batch culture was carried out by employing the same cells and culture conditions as in Example 1, except that no removal of culture supernatant by centrifugation was conducted.

Figure 8A:
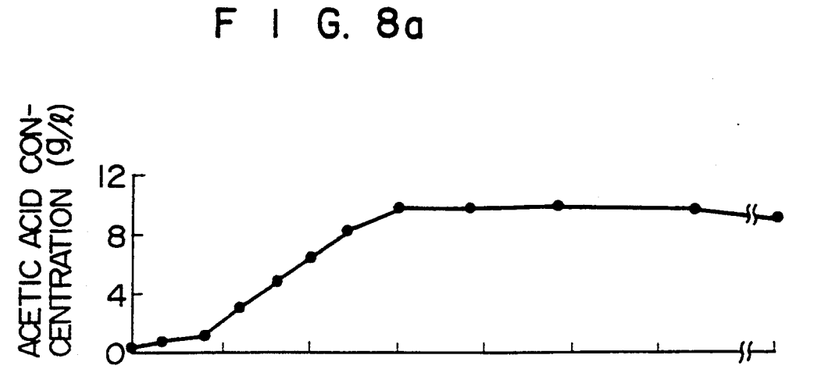
FIG. 8 shows the results of comparative example of fed-batch culture of recombinant *E. coli*.
Figure 8B:
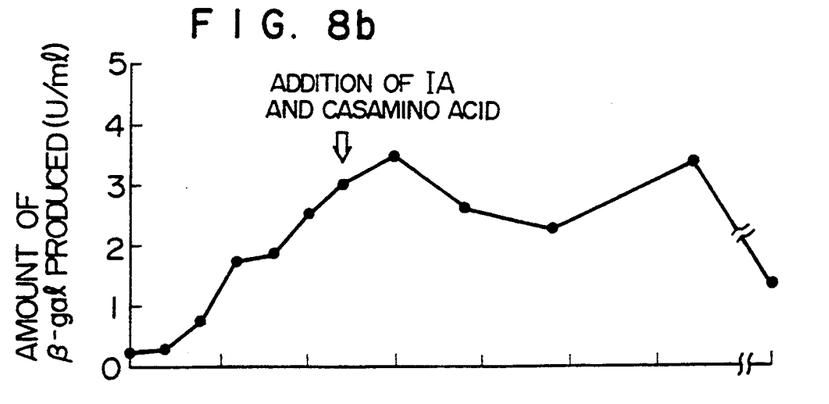
Figure 8C:
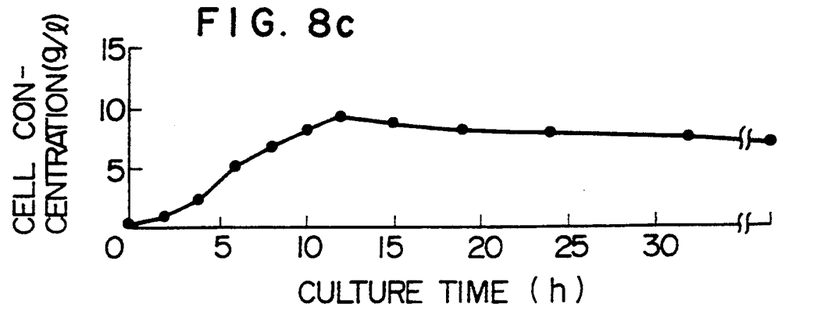

Results: As shown in FIG. 8, 50 mg/liter of IA and 25 g/liter of casamino acid were added at 12 hours of culture at which the cell concentration become 9.5 g/liter and the acetic acid concentration 8.2 g/liter, but no $\beta$-gal. production was induced.

What is claimed is:

1. A process for producing a desired protein by culturing a transformed *E. coli*, containing exogenous DNA comprising a trp promotor which regulates expression of an exogenous gene encoding a desired protein wherein expression of said gene is inhibited by acetic acid, which comprises the sequential steps of:
- (a) growing the transformed *E. coli* in a culture broth without inducing expression of the exogenous gene encoding the desired protein, monitoring acetic acid concentration and allowing acetic acid to accumulate to less than 17 g/l;
- (b) maintaining the concentration of acetic acid during the growing step at less than 17 g/l by removing acetic acid from the culture broth or diluting the culture broth to an acetic acid concentration of less than 17 g/l;
- (c) reducing the concentration of acetic acid to less than 3 g/l by removing acetic acid from the culture broth or diluting the culture medium, to below the acetic acid concentration maintained above;
- (d) adding both an agent inducing expression of the gene encoding the desired protein, and, nutrient into the culture broth to produce the desired protein;
- (e) maintaining the concentration of acetic acid in step (c) above in the culture broth at less than 3 g/l; and
- (f) recovering the desired protein.

2. The process according to claim 1, wherein the nutrient does not contain tryptophan.

3. The process according to claim 1, wherein an inhibitor of the trp promotor is present in the culture broth during steps (a) and (b).

4. The process according to claim 1, wherein the *E. coli* is cultured under aerobic conditions.

* * * * *